(12) United States Patent
Almstead et al.

(10) Patent No.: US 8,367,841 B2
(45) Date of Patent: *Feb. 5, 2013

(54) PROCESSES FOR THE PREPARATION OF 1,2,4-OXADIAZOLE BENZOIC ACIDS

(75) Inventors: Neil G. Almstead, Princeton, NJ (US); Peter Seongwoo Hwang, Edison, NJ (US); Seemon Pines, New Providence, NJ (US); Young-Choon Moon, Belle Mead, NJ (US); James J. Takasugi, Lawrenceville, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 479 days.

This patent is subject to a terminal disclaimer.

(21) Appl. No.: 12/617,757

(22) Filed: Nov. 13, 2009

(65) Prior Publication Data

US 2010/0063297 A1     Mar. 11, 2010

Related U.S. Application Data

(62) Division of application No. 11/899,813, filed on Sep. 6, 2007, now Pat. No. 7,678,922.

(60) Provisional application No. 60/843,595, filed on Sep. 8, 2006.

(51) Int. Cl.
*C07D 271/06* (2006.01)
(52) U.S. Cl. .......................................... 548/131; 548/125
(58) Field of Classification Search .................. 548/125, 548/131

See application file for complete search history.

(56) References Cited

U.S. PATENT DOCUMENTS

| | | | | |
|---|---|---|---|---|
| 7,304,080 B2 * | 12/2007 | Karp et al. | ..................... | 514/364 |
| 7,419,991 B2 * | 9/2008 | Karp et al. | ..................... | 514/364 |
| 7,678,922 B2 * | 3/2010 | Almstead et al. | ............. | 548/131 |

* cited by examiner

*Primary Examiner* — Golam M M Shameem
(74) *Attorney, Agent, or Firm* — Jones Day

(57) ABSTRACT

Provided herein are processes for the preparation of compounds useful for the treatment, prevention or management of diseases associated with a nonsense mutation. More specifically, provided herein are processes for the synthesis of 1,2,4-oxadiazoles. In particular, provided herein are processes useful for the preparation of 3-[5-(2-fluorophenyl)-[1,2,4] oxadiazol-3-yl]-benzoic acid.

8 Claims, No Drawings

PROCESSES FOR THE PREPARATION OF 1,2,4-OXADIAZOLE BENZOIC ACIDS

This application is a division of U.S. application Ser. No. 11/899,813, filed Sep. 6, 2007, now U.S. Pat. No. 7,678,922 currently allowed, which claims the benefit of U.S. provisional application No. 60/843,595, filed Sep. 8, 2006, the disclosures of which are incorporated by reference herein in their entirety.

1. FIELD

Provided herein are processes for the preparation of compounds useful for the treatment, prevention or management of diseases associated with a nonsense mutation. More specifically, provided herein are processes for the synthesis of 1,2,4-oxadiazoles. In particular, provided herein are processes useful for the preparation of 3-[5-(2-fluorophenyl)-[1,2,4]oxadiazol-3-yl]-benzoic acid.

2. BACKGROUND 1,2,4-oxadiazole compounds useful for the treatment, prevention or management of diseases ameliorated by modulation of premature translation termination or nonsense-mediated mRNA decay are described in U.S. Pat. No. 6,992,096 B2, issued Jan. 31, 2006, which is incorporated herein by reference in its entirety. One such compound is 3-[5-(2-fluorophenyl)-[1,2,4]oxadiazol-3-yl]-benzoic acid.

Existing solution phase methods for synthesizing 1,2,4-oxadiazole benzoic acids are described in U.S. Pat. No. 6,992,096 B2, issued Jan. 31, 2006 (see column 57, line 40, Scheme B, and Example 2). In particular, these methods comprise multiple reactions steps, each followed by isolation of the desired intermediate.

While these methods are enabling and useful for preparing 1,2,4-oxadiazole benzoic acids, there are possibilities for alterations that may result in a more efficient synthesis. In particular, synthetic processes with fewer isolation steps and which may comprise the use of fewer solvents can be more efficient and less expensive.

Citation of any reference in Section 2 of this application is not to be construed as an admission that such reference is prior art to the present application.

3. SUMMARY

Provided herein are processes useful for the production of 1,2,4-oxadiazole benzoic acids that are efficient, cost effective and readily scaleable with commercial reagents.

In one embodiment, provided herein are processes useful for preparing a 1,2,4-oxadiazole benzoic acid comprising the steps of: (1) reacting a cyanobenzoate ester with hydroxylamine; (2) acylation with a halobenzoyl chloride; (3) condensation; and (4) hydrolysis of the benzoate ester.

In a particular embodiment, steps (1)-(3) are carried out in the same organic solvent.

In another particular embodiment, steps (1)-(3) are carried out in a single organic solvent.

In another embodiment, steps (1)-(4) are carried out in the same organic solvent.

In another embodiment, steps (1)-(4) are carried out in a single organic solvent.

In another embodiment, steps (1)-(3) are carried out in the same aqueous solvent.

In another embodiment, steps (1)-(3) are carried out in a single aqueous solvent.

In another embodiment, steps (1)-(4) are carried out in the same aqueous solvent.

In another embodiment, steps (1)-(4) are carried out in a single aqueous solvent.

In another embodiment, steps (1)-(3) are carried out without isolation of an intermediate.

In another embodiment, steps (1)-(4) are carried out without isolation of an intermediate.

In another embodiment, steps (1)-(4) are followed by a micronization step.

In still another embodiment, the processes provided herein are useful for preparing 1,2,4-oxadiazole benzoic acids and pharmaceutically acceptable salts, hydrates, solvates, or polymorphs thereof. In yet another embodiment, the processes provided herein are useful for preparing 1,2,4-oxadiazole benzoic acids and pharmaceutically acceptable salts, hydrates, solvates, or polymorphs thereof useful for treating, preventing or managing diseases or conditions associated with a nonsense mutation. In yet another embodiment, the processes provided herein are useful for preparing 1,2,4-oxadiazole benzoic acids and pharmaceutically acceptable salts, hydrates, solvates, or polymorphs thereof useful for treating preventing or managing genetic diseases and disorders.

4. DETAILED DESCRIPTION OF THE INVENTION

4.1 Terminology

As used herein and unless otherwise indicated, the term "halo", "halogen", or the like means —F, —Cl, —Br, or —I.

Unless otherwise indicated, the compounds described herein, including intermediates useful for the preparation of the compounds, which contain reactive functional groups (such as, without limitation, carboxy, hydroxy, and amino moeties) also include protected derivatives thereof "Protected derivatives" are those compounds in which a reactive site or sites are blocked with one or more protecting groups (also known as blocking groups). Suitable protecting groups for carboxy moieties include benzyl, t-butyl, and the like. Suitable protecting groups for amino and amido groups include acetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in T. W. Green, "Protective Groups in Organic Synthesis", Third Ed., Wiley, New York, 1999, which is incorporated herein by reference in its entirety.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "process(es)" refers to the methods disclosed herein which are useful for preparing a 1,2,4-oxadiazole benzoic acid compound.

As used herein and unless otherwise indicated, the terms "adding" or "addition" or the like mean contacting one reactant, reagent, solvent, catalyst, or the like with another reactant, reagent, solvent, catalyst, or the like. Reactants, reagents, solvents, catalysts, or the like can be added individually, simultaneously, or separately and can be added in any order. They can be added in the presence or absence of heat and can optionally be added under an inert atmosphere.

As used herein and unless otherwise indicated, a reaction that is "substantially complete" or is driven to "substantial completion" means that the reaction contains more than about 80% by percent yield, more than about 90% by percent yield, more than about 95% by percent yield, or more than about 97% by percent yield of the desired product.

As used herein and unless otherwise indicated, the term "without isolation" means that the reaction mixture resulting from one step is carried through to a subsequent step without isolating the desired product. In certain embodiments, performing multiple reaction steps "without isolation" includes processes which comprise transferring the reaction mixture resulting from one step into a new reaction vessel prior to beginning a subsequent reaction.

As used herein and unless otherwise indicated, the term "condensation" means a chemical reaction in which two chemical moieties react and become covalently bonded to one another with concurrent loss of a small molecule, for example, water.

As used herein and unless otherwise indicated, the term "pharmaceutically acceptable salt" refers to a salt of compound of the present invention that is safe and effective for use in a patient. Exemplary pharmaceutically acceptable salts are prepared using metals, inorganic bases or organic bases. Suitable base salts include, but are not limited to, aluminum, calcium, lithium, magnesium, potassium, sodium, ammonium and zinc salts. A suitable organic base salt is triethylamine.

As used herein and unless otherwise indicated, the term "hydrate" means a compound of the present invention or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound of the present invention. The term "solvate" includes hydrates (e.g., hemihydrate, mono-hydrate, dihydrate, trihydrate, tetrahydrate, and the like).

As used herein and unless otherwise indicated, the term "polymorph" means solid crystalline forms of a compound of the present invention or complex thereof. Different polymorphs of the same compound may exhibit different physical, chemical and/or spectroscopic properties.

As used herein and unless otherwise indicated, the phrase "diseases or disorders associated with a nonsense mutation" means diseases or disorders that would not arise, endure, or cause symptoms if the nonsense mutation was not present.

As used herein and unless otherwise indicated, the term "treat," "treatment," "treating," or the like refers to the reduction or amelioration of the progression, severity and/or duration of a disease or disorder, or the amelioration of one or more symptoms (preferably, one or more discernible symptoms) of a disease or condition resulting from the administration of one or more therapies (e.g., one or more therapeutic agents such as a 1,2,4-oxadiazole benzoic acid).

As used herein and unless otherwise indicated, the term "prevent," "prevention," "preventing," or the like refers to the reduction in the risk of acquiring or developing a given disease or disorder, or the reduction or inhibition of the recurrence, onset, or development of one or more symptoms of a given disease or disorder.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

The embodiments provided herein can be understood more fully by reference to the following detailed description and illustrative examples, which are intended to exemplify non-limiting embodiments.

4.2 Processes

Provided herein are cost-effective and efficient processes useful for the production of 1,2,4-oxadiazole benzoic acids.

In one embodiment, the processes comprise the use of m-cyanobenzoic acid methyl ester.

In another embodiment, the processes comprise the use of fluorobenzoyl chloride.

In another embodiment, the processes comprise the use of o-fluorobenzoyl chloride.

In another embodiment, steps (1)-(3) are carried out in a single organic solvent or the same organic solvent and without isolation of an intermediate between the steps.

In another embodiment, steps (1)-(4) are carried out in a single organic solvent or the same organic solvent and without isolation of an intermediate between steps (1)-(3).

In another embodiment, steps (1)-(4) are carried out in a single organic solvent or the same organic solvent and without isolation of an intermediate between steps (1)-(4).

In another embodiment, steps (1)-(3) or steps (1)-(4) are carried out in a single aqueous solvent or the same aqueous solvent and without isolation of an intermediate between steps (1)-(3) or, in another embodiment, steps (1)-(4).

In one embodiment, the solvent used in the processes described herein is a polar solvent such as tetrahydrofuran, dioxane, isobutyl acetate, isopropyl acetate, and ethyl acetate.

In another embodiment, the solvent used in the processes described herein is a alcoholic solvent such as methanol, ethanol, isopropanol, isobutanol, propanol, butanol, and tent-amyl alcohol.

In another embodiment, the solvent used in the processes described herein is tent-butanol.

In one embodiment, the processes described herein are useful for producing a batch size of a 1,2,4-oxadiazole benzoic acid of about 500 mg or more, about 1 kg or more, about 5 kg or more, about 10 kg or more, about 25 kg or more, about 50 kg or more, about 75 kg or more, about 100 kg or more, about 125 kg or more, about 150 kg or more, about 175 kg or more, about 200 kg or more, about 225 kg or more, about 250 kg or more, about 275 kg or more, about 300 kg or more, about 325 kg or more, about 350 kg or more, about 375 kg or more, about 400 kg or more, about 425 kg or more, about 450 kg or more about 475 kg or more, or about 500 kg, or about 600 kg, or about 700 kg, or about 800 kg or about 900 kg, or about 1000 kg or more.

In one embodiment, the 1,2,4-oxadiazole benzoic acid is produced in one of the above described batch sizes in an overall yield of about 50% or more, about 55% or more, about 60% or more, about 65% or more, about 70% or more, about 75% or more, about 80% or more, about 85% or more, about 90% or more, or about 95% or more.

In one embodiment, steps (1)-(4) are followed by a micronization step. In a particular embodiment, the micronized 1,2,4-oxadiazole benzoic acid has a particle size distribution of $D(v,0.1)$: about 0.5 μm to about 1.0 μm; $D(v,0.5)$: about 1.5 μm to about 5.0 μm; and $D(v,0.9)$: about 5.5 μm to about 10.0 μm.

In one embodiment, provided herein are processes useful for preparing a compound of formula I:

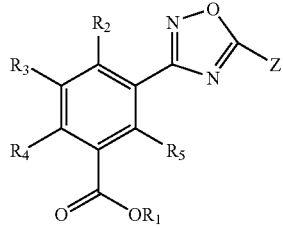

or pharmaceutically acceptable salts, hydrates, clathrates, prodrugs, polymorphs, stereoisomers, including enantiomers, diastereomers, racemates or mixtures of stereoisomers, thereof, wherein:

Z is substituted or unsubstituted aryl, substituted or unsubstituted heteroaryl, substituted or unsubstituted cycloalkyl, substituted or unsubstituted alkyl, substituted or unsubstitued alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, $-(CH_2CH_2O)_nR^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$; and n is an integer from 1 to 7, which comprises the steps of:

(1) reacting an optionally substituted cyanobenzoate ester with hydroxylamine;

(2) acylation with an acid chloride;

(3) condensation; and (4) optional hydrolysis of the benzoate ester.

In one embodiment, steps (1)-(3) are carried out in a single organic solvent.

In another embodiment, steps (1)-(3) are carried out in the same organic solvent.

In another embodiment, steps (1)-(4) are carried out in a single organic solvent.

In another embodiment, steps (1)-(4) are carried out in the same organic solvent.

In another embodiment, steps (1)-(3) are carried out without isolation of an intermediate.

In another embodiment, steps (1)-(4) are carried out without isolation of an intermediate.

In another embodiment, steps (1)-(3) are carried out in a single organic solvent or the same organic solvent and without isolation of an intermediate between the steps.

In another embodiment, steps (1)-(4) are carried out in a single organic solvent or the same organic solvent and without isolation of an intermediate between steps (1)-(3).

In another embodiment, steps (1)-(4) are carried out in a single organic solvent or the same organic solvent and without isolation of an intermediate between steps (1)-(4).

In one embodiment, the solvent used in the processes described herein is tert-butanol.

In one embodiment, the processes provided herein are useful for preparing a compound of formula I having the structure of formula II:

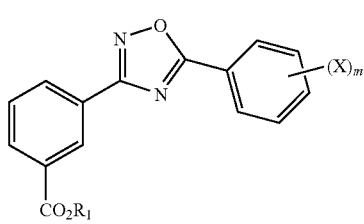

or pharmaceutically acceptable salts, hydrates, clathrates, prodrugs, polymorphs, stereoisomers, including enantiomers, diastereomers, racemates or mixtures of stereoisomers, thereof, wherein:

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, $-(CH_2CH_2O)_nR^6$ or any biohydrolyzable group;

X is at each occurrence independently F, Cl, Br or I; and m is an integer from 1 to 5, which comprises the steps of:

(1) reacting a cyanobenzoic acid methyl ester with hydroxylamine;

(2) acylation with a halobenzoyl chloride;

(3) condensation; and (4) hydrolysis of the methyl ester.

In one embodiment, X is F.

In another embodiment, m is 1.

In another embodiment, X is F and m is 1.

In another embodiment, m is 1 and X is F in the ortho position.

In another embodiment, m is 1 and X is F in the meta position.

In another embodiment, m is 1 and X is F in the para position.

In another embodiment, $R_1$ is H.

In one embodiment, provided herein are processes for preparing compounds of formula I, including compounds having the structure of formulas II and IIa, comprising the steps set forth in Scheme 1:

Scheme 1

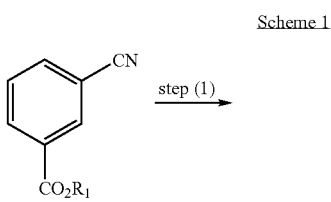

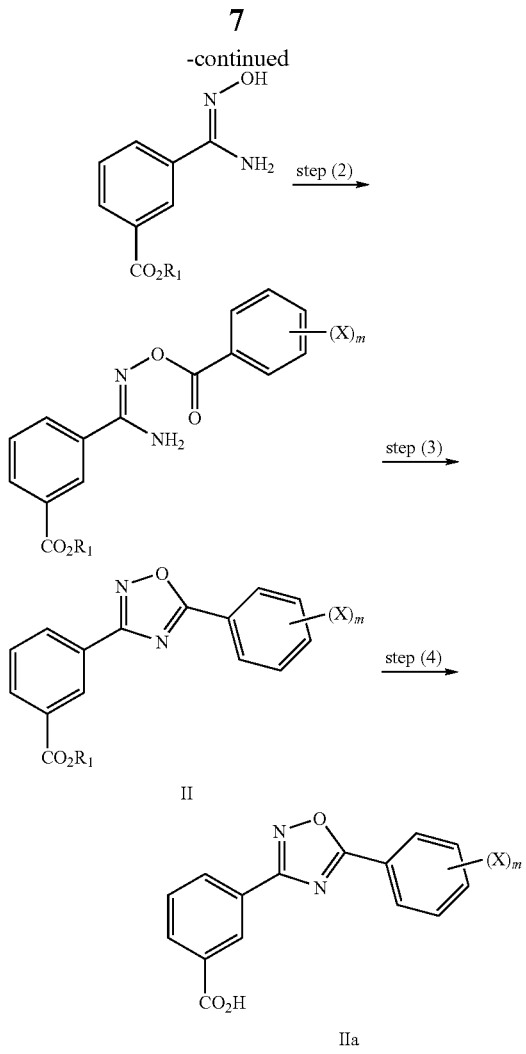

wherein $R_1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —$(CH_2CH_2O)_nR^6$, any biohydrolyzable group or any suitable blocking group know to one skilled in the art, wherein step (4) is an optional hydrolysis step when $R_1$ is other than H;

X is at each occurrence independently F, Cl, Br or I; and m is an integer from 1 to 5.

In one embodiment of Scheme 1, X is F.

In another embodiment of Scheme 1, m is 1.

In another embodiment of Scheme 1, X is F and m is 1.

In another embodiment, m is 1 and X is F in the ortho position.

In another embodiment, m is 1 and X is F in the meta position.

In another embodiment, m is 1 and X is F in the para position.

In another embodiment of Scheme 1, $R_1$ is methyl.

In another embodiment of Scheme 1, steps (1)-(3) are carried out in a single organic solvent.

In another embodiment of Scheme 1, steps (1)-(3) are carried out in the same organic solvent.

In another embodiment of Scheme 1, steps (1)-(4) are carried out in a single organic solvent.

In one embodiment of Scheme 1, steps (1)-(4) are carried out in the same organic solvent.

In another embodiment of Scheme 1, steps (1)-(3) are carried out without isolation of an intermediate.

In another embodiment of Scheme 1, steps (1)-(4) are carried out without isolation of an intermediate.

In another embodiment of Scheme 1, steps (1)-(3) are carried out in a single organic solvent or the same organic solvent and without isolation of an intermediate between the steps.

In another embodiment of Scheme 1, steps (1)-(4) are carried out in a single organic solvent or the same organic solvent and without isolation of an intermediate between steps (1)-(3).

In another embodiment, steps (1)-(4) are carried out in a single organic solvent or the same organic solvent and without isolation of an intermediate between steps (1)-(4).

In one embodiment of Scheme 1, the solvent used is tetrahydrofuran, dioxane, isobutyl acetate, isopropyl acetate, ethyl acetate, methanol, ethanol, isopropanol, isobutanol, propanol, butanol or tent-amyl alcohol.

In a particular embodiment of Scheme 1, the solvent used is tert-butanol.

In one embodiment of Scheme 1, step (1) comprises reacting 3-cyanobenzoic acid methyl ester with aqueous hydroxylamine in tert-butanol. In a particular embodiment, 50% aqueous hydroxylamine is used in step (1). In another embodiment, molten tert-butanol is used in step (1). In another embodiment, the aqueous hydroxylamine is added to the 3-cyanobenzoic acid methyl ester and tert-butanol at about 40-45° C. In another embodiment, the reaction mixture of step (1) is stirred for about 2 hours.

In another embodiment of Scheme 1, step (2) comprises reacting the product from step (1) with a halobenzoyl chloride in triethylamine and tert-butanol. In a particular embodiment, the halobenzoyl chloride is fluorobenzoyl chloride, more particularly, 2-fluorobenzoyl chloride. In another embodiment, the reaction mixture of step (2) is further diluted with molten tert-butanol. In another embodiment, the reaction of step (2) is carried out at a temperature of less than 40° C., and in a particular embodiment, at about 30-35° C.

In another embodiment, the reaction mixture of step (2) is stirred for at least about 2 hours. In certain embodiments, additional triethylamine or halobenzoyl chloride can be added to the reaction mixture of step (2) to drive the reaction to completion.

In another embodiment of Scheme 1, step (3) comprises refluxing the product from step (2) in tert-butanol. In a particular embodiment, step (3) comprises refluxing the product from step (2) in tert-butanol at about 82° C. In another embodiment, step (3) comprises crystallizing the ring-closed product by the addition of water at about 60-65° C. In another embodiment, the resulting slurry is cooled to room temperature, filtered, washed with tent-butanol/water (50/50 v/v) and dried in vacuo.

In another embodiment of Scheme 1, step (4) comprises hydrolyzing the methyl ester of the product from step (3) into the corresponding sodium salt by the addition of aqueous sodium hydroxide in tert-butanol. In one embodiment, hydrolysis of methyl ester of the product from step (3) is carried out in aqueous sodium hydroxide and tert-butanol at about 68-72° C. In a further embodiment, step (4) comprises converting the sodium salt to the free acid by filtering hot sodium salt solution through an in-line filter (e.g., a 5 micron in-line filter) and acidifying with sulfuric acid to about pH 1-3. In a still further embodiment, step (4) comprises converting the sodium salt to the free acid by filtering hot sodium salt solution through an in-line filter (e.g., a 1 micron in-line filter) and acidifying with about 10-15% hydrochloric acid to about pH 1-3 followed by stirring at about 70° C. for about 1 hour. In a further embodiment, the free acid is isolated using a Rosenmund filter and washed with aqueous tert-butanol and water, followed by drying (e.g., with a paddle dryer or double-cone dryer) or centrifuging.

The progress of reactions described herein can be monitored by any method known to one skilled in the art including, but not limited to, thin-layer chromatography (TLC), high-performance liquid chromatography (HPLC), or spectroscopic methods (e.g., $^1$H-NMR, $^{13}$C-NMR, IR, Raman, MS).

In one embodiment, provided herein are processes for preparing 3-[5-(2-fluorophenyl)-[1,2,4]oxadiazol-3-yl]-benzoic acid, comprising the steps set forth in Scheme 2:

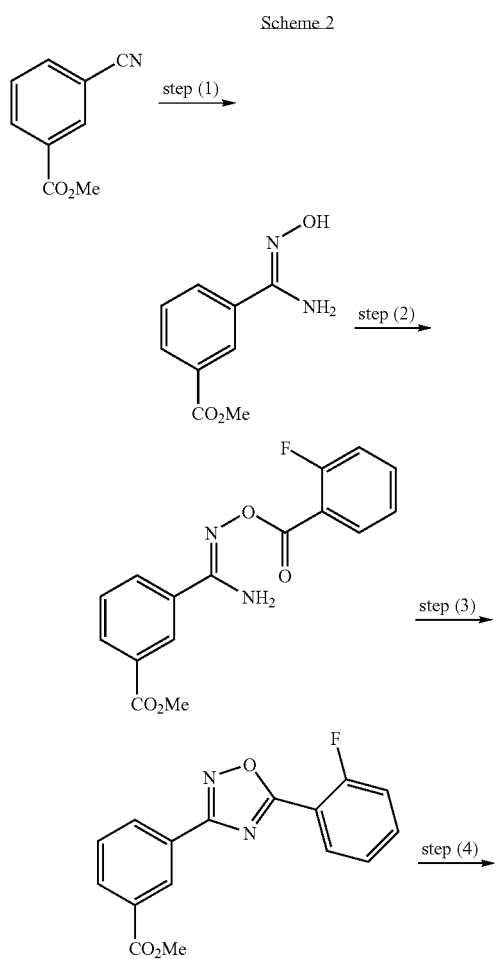

In one embodiment, provided herein are processes useful for preparing a compound of formula II, comprising performing the following steps:

(1) reacting the cyanobenzoic acid methyl ester:

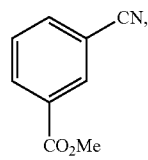

with hydroxylamine, to give:

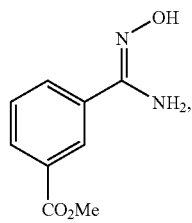

followed by (2) acylation with a halobenzoyl chloride, to give:

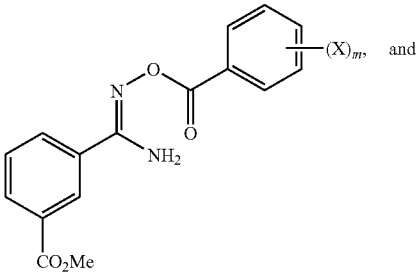

followed by (3) condensation to give:

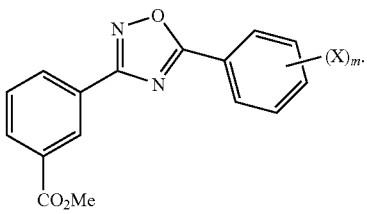

In another embodiment, the processes provided herein further comprise (4) hydrolysis of the methyl ester to give:

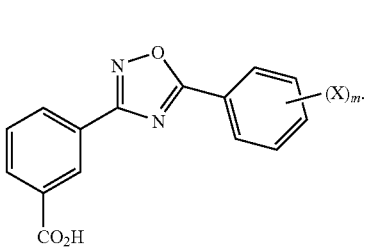

In one embodiment, X is F.
In another embodiment, m is 1.
In another embodiment, X is F and m is 1.

In another embodiment, m is 1 and X is F in the ortho position.

In another embodiment, m is 1 and X is F in the meta position.

In another embodiment, m is 1 and X is F in the para position.

In another embodiment, steps (1)-(3) are carried out in a single organic solvent.

In another embodiment, steps (1)-(3) are carried out in the same organic solvent.

In another embodiment, steps (1)-(4) are carried out in a single organic solvent.

In another embodiment, steps (1)-(4) are carried out in the same organic solvent.

In another embodiment, steps (1)-(3) or steps (1)-(4) are carried out in tert-butanol.

In another embodiment, steps (1)-(3) are carried out without isolation of an intermediate.

In another embodiment, steps (1)-(4) are carried out without isolation of an intermediate.

In another embodiment, steps (1)-(3) or steps (1)-(4) are carried out in a single organic solvent or the same organic solvent and without isolation of an intermediate.

In one embodiment, the solvent used is tetrahydrofuran, dioxane, isobutyl acetate, isopropyl acetate, ethyl acetate, methanol, ethanol, isopropanol, isobutanol, propanol, butanol or tent-amyl alcohol.

In a particular embodiment, the solvent used is tent-butanol.

In one embodiment, the compound of formula II is 3-[5-(2-fluorophenyl)-[1,2,4]oxadiazol-3-yl]-benzoic acid.

In another embodiment, the synthesis is carried out in a single reaction vessel (i.e., a "one pot" synthesis).

In one embodiment, provided herein are processes useful for preparing a compound of formula II, comprising performing the following steps in a single reaction vessel:

reacting cyanobenzoic acid:

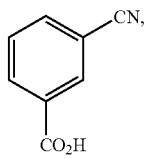

with hydroxylamine, to give:

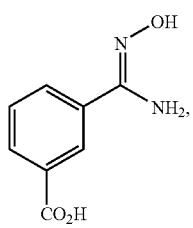

followed by acylation with a halobenzoyl chloride, to give:

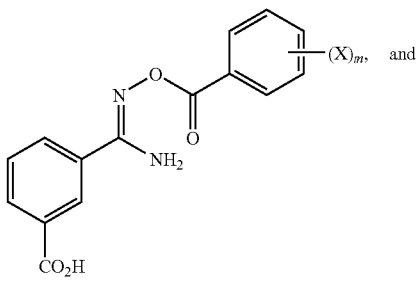

followed by reflux to give:

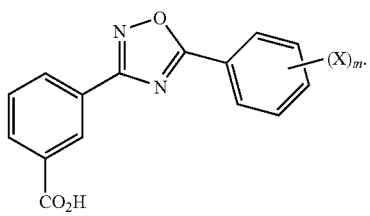

In one embodiment, the compound is 3-[5-(2-fluorophenyl)-[1,2,4]oxadiazol-3-yl]-benzoic acid.

The embodiments described herein are further illustrated by the examples set forth below, which are not to be construed as limiting the scope of the embodiments described herein.

Starting materials and reagents useful in the processes described herein can be obtained from commercial sources or prepared using methods known to one skilled in the art.

5. EXAMPLES

Methyl 3-[5-(2-fluorophenyl)-[1,2,4]oxadiazol-3-yl]-benzoate

Batch 1

Methyl 3-cyanobenzoate (105 kg) and molten tert-butanol were charged to a dry reactor. 50% aqueous hydroxylamine (43 L, 47.4 kg) was added to the clear solution of methyl 3-cyanobenzoate in molten tert-butanol in an inert atmosphere over about 2 hours and 48 minutes. The maximum batch temperature during the addition of 50% aqueous hydroxylamine was about 43° C. The addition rate of 50% aqueous hydroxylamine varied from about 9 L per hour at the onset of addition to about 30 L per hour. The batch temperature was maintained by alteration of the jacket set point on the reactor. In particular, the set point was changed from about 40.5° C. at the beginning of the addition to about 29.6° C. as the addition rate increased. The reaction was deemed complete (i.e., less than about 0.5% ester) after stirring for about 4 hours at about 40-45° C.

The batch was transferred to a dry reactor and chased through with about 10 L of molten tert-butanol. The jacket set point was decreased from about 33° C. when the batch was received by the dry reactor to about 27° C. after transfer was complete. Partial crystallization of the batch was observed which did not adversely affect stirring. The batch was cooled to about 34.4° C. and triethylamine (72.6 kg, 100 L) was charged to the reactor. The jacket temperature set point was raised from about 20.4° C. to about 31.0° C. to maintain the batch temperature with the range of about 30-35° C. Following a line rinse with molten tert-butanol (10 L), the batch was charged with 2-fluorobenzoyl chloride (113.7 kg, 86.0 L). The addition rate over the first third of the charge was about 25 L per hour. The jacket inlet temperature was lowered to about 15° C. during this period and the batch temperature remained at about 34.6° C. The addition was complete after about 5.5 hours. The maximum batch temperature during the addition was about 38.8° C. The addition rate was slowed towards the end of the addition with the final 27 liters of 2-fluorobenzoyl being added at about 11 L per hour. The reaction was deemed complete (i.e., less than about 0.5% methyl 3-amidinobenzoate) after stirring for about 2 hours at 30-35° C.

The batch was then heated to reflux temperature (about 82° C.) over about 1 hour and 42 minutes and stirred for about an additional 18 hours. During stirring, some product partially crystallized to form a slurry. The slurry was cooled to bout 40° C. to allow for sampling, during which full crystallization occurred. The batch was reheated to reflux temperature and stirred for about 1 hour and 50 minutes. The batch was then cooled over about 2 hours to about 69° C. and 630 L of purified water was slowly added over about 4 hours and 15 minutes while the batch temperature was maintained at between about 66-69° C. The slurry was cooled to about 22.4° C. over about 3 hours and 14 minutes and transferred to 2×200 L ceramic filters fitted with 25-30µ mesh polypropylene filter cloths. Transfer of the material from the vessel onto the filters was complete after about 55 minutes. The filter cakes were washed with 50% aqueous tert-butanol (210 L), allowing about 10 minutes for the wash to soak into each cake. The cakes were then dried in vacuo over about 5-10 minutes. Purified water was applied to the filter cakes as a secondary wash (158 L per cake) to remove residual tert-butanol and triethylammonium chloride salt. Liquors were removed after drying in vacuo for about 5 minutes. The cakes were dried in vacuo for about an additional 2 hours and then sampled using liquid chromatography. The purity of the cakes was determined to be about 99.6% by liquid chromatography.

After drying the cakes in vacuo for about 8 hours and 25 minutes, the wet cake (207.4 kg) was transferred to an air oven. Drying in the air oven was performed at about 50-55° C. for about 52 hours. The overall yield of isolated product was about 89.9% (174.65 kg), which can be adjusted to about 90.7% after accounting for material consumed by sampling.

Batch 2

Methyl 3-cyanobenzoate (105 kg) and molten tert-butanol were charged to a dry reactor. 50% aqueous hydroxylamine (47.85 kg) was charged to the reactor in an inert atmosphere over about 3 hours and 29 minutes. The temperature was maintained at about 40-45° C. during addition. The reaction was deemed complete (i.e., less than about 0.5% ester) after stirring for about 3 hours and 16 minutes at about 40-45° C.

The batch was transferred to a dry reactor as described for Batch 1. The batch was cooled to about 34.4° C. and charged with triethylamine (72.6 kg, 100 L). The addition was performed over a period of about 45 minutes while maintaining the batch temperature at about 30-35° C. The jacket inlet temperature was raised from about 31.4° C. to about 32.6° C. during the addition. After line rinse with molten tert-butanol, the batch was charged with 2-fluorobenzoyl chloride (113.7 kg, 86.0 L). The acid chloride was added over about 3 hours and 27 minutes. After stirring for about 8 hours at 35° C., the reaction was deemed not to be complete (i.e., more than about 0.5% of methyl 3-amidinobenzoate remained). 1.5% by weight of the original charges of triethylamine and 2-fluorobenzoyl chloride were then added to the batch. Each of the additional charges were accompanied by a line rinse of tert-butanol (10 L). No additional cooling was performed during the addition of the acid chloride. The batch temperature was maintained at about 30-35° C. with the jacket inlet temperature ranging from about 30.3° C. to about 33.0° C. The reaction was deemed complete (i.e., less than about 0.5% methyl 3-amidinobenzoate) after stirring for about 2 hours at 30-35° C.

The batch was heated to reflux temperature (about 83° C.) over about 1 hour and 44 minutes and stirred for about 18 hours. As with Batch 1, solids fully crystallized during cooling for sampling. The batch was reheated to reflux temperature and stirred for about 1 hour and 2 minutes. The batch was then cooled over about 2 hours and 20 minutes to about 69.2° C. and 630 L of purified water was slowly added over about 4 hours and 30 minutes while the batch temperature was maintained at between about 65.6-69.2° C. The slurry was cooled to about 23.4° C. over about 3 hours and 30 minutes and the contents were transferred to dual ceramic filters as described for Batch 1. The transfer of material was complete after about 5 hours and 6 minutes. The filter cakes were washed with about 50% aqueous tert-butanol (2 volumes per cake) allowing 10 minutes for the wash to soak into each cake prior to drying in vacuo. Filtration was complete after about 1 hour and 40 minutes. Purified water was applied to the cakes as the final wash. Liquors were removed by drying in vacuo for about 10 minutes. The cakes were dried in vacuo for about an additional 2 hours and 5 minutes and then sampled using liquid chromatography. The purity of the cakes were determined to be about 99.5% and 99.6%, respectively, by liquid chromatography.

After drying the cakes in vacuo for about an additional 2 hours and 5 minutes, the wet cake (191.5 kg) was transferred to an air oven. Drying in the air oven was performed at about 50-55° C. for about 48 hours. The overall yield of isolated product was about 92.5% (179.7 kg).

Batch 3

A reaction vessel was charged with 3-cyanobenzoic acid methyl ester (52.5 kg) and molten tert-butanol (228 kg). The vessel was sealed and the batch temperature was set to about 40-45° C. and the agitator was started. 50% Aqueous hydroxylamine (24 kg) was charged to the reactor in an inert atmosphere over 2 hours and 40 minutes. The temperature was maintained at about 40-45° C. during the addition. The reaction was complete after stirring for about an additional 5 hours at about 42° C.

The batch was cooled to 30-35° C. and charged with triethylamine (36 kg) over 15 minutes. 2-Fluorobenzoyl chloride (57 kg) was added over about 2 hours and 44 minutes. The batch temperature was maintained at about 30-35° C. during the addition. The batch was stirred for a further 2 hours and 10 minutes at 32° C. and the reaction was complete.

The batch was heated to reflux temperature (about 83-86° C.) over about 50 minutes and stirred for about 18 hours at about 81° C. The batch was then cooled over about 2 hours to about 65-70° C. and purified water (315 L) was slowly added over about 6 hours and 25 minutes while the batch temperature was maintained at between about 65-70° C. The slurry was cooled to about 22° C. over about 2 hours and 15 minutes and the contents were transferred to a centrifuge filter (2 batches). Filtration was complete after about 1 hours and 40 minutes. The filter cakes were washed with about 50% aqueous tert-butanol (90 kg per cake) over about 20 minutes. Purified water (79 kg per cake) was applied to the cakes as the final wash. The cakes were dried at about 900 rpm for about 1 hour and 5 minutes and then discharged in to a drum. The purity of the wet cake (91.5 kg, LOD=5% w/w) was determined to be about 99.75% area, by liquid chromatography.

3-[5-(2-fluorophenyl)-[1,2,4]oxadiazol-3-yl]-benzoic acid

Batch 1

A reaction vessel was charged with methyl 3-[5-(2-fluorophenyl)-[1,2,4]oxadiazol-3-yl]-benzoate (74.0 kg), the vessel was sealed, evacuated and purged. The jacket set-point was set to about 35° C. and the agitator was started in the vessel. Molten tert-butanol (222 L, 3 vol.) and purified water (355 L, 4.8 vol.) were charged into the vessel. These charges were followed by the addition of 25.1% w/w aqueous sodium hydroxide solution (43.5 kg, 1.1 mol equiv.) and a line rinse with additional purified water (100 L, 1.35 mol). The batch temperature dropped from about 39.0° C. to about 38.8° C. during the addition. The batch temperature was raised to about 63-67° C. over about 1 hour and 54 minutes and then adjusted to about 68-72° C. over about 30 minutes. The mixture was stirred for about 3 hours at about 68-72° C. The solution was then cooled to about 40-45° C. over about 5 hours and 11 minutes. The solution was then reheated to about 68-72° C. following the above procedure over about 3 hours and 33 minutes.

The jacket temperature on the reaction vessel was set to about 60° C., the agitator was started and the hot liquor was transferred through a 1 micron filter at about 70° C. under slight positive pressure of nitrogen (1.5 to 5.6 psig). The product temperature dropped to about 64.3° C. during the transfer, which was completed in about 45 minutes. The vessel was charged with purified water (61 L, 0.82 vol.) and the contents were heated to about 68-72° C.

The batch temperature was adjusted to about 69.4° C. and treated with 13.9% w/w sulfuric acid (100.7 kg, 1.15 mol equiv.) over about 4 hours and 18 minutes. The batch temperature was maintained at about 68.0-70.8° C. during the addition. Acid addition was followed by a line rinse with purified water (50L, 0.68 vol.) and stirring at about 68-72° C. was continued for about an additional 31 minutes.

The batch was cooled in a linear fashion from about 69.2° C. to about 41.2° C. over about 4 hours and 10 minutes. The stirrer on a Rosenmund filter/dryer was raised to the highest position and the jacket set point was set at about 40° C. The slurry was transferred into the filter/dryer in two parts. Constant nitrogen pressure was applied to the first part (less than about 15 psig). The pressure ranged from about 23.9 to about 28.8 psi during the transfer, which was completed in about 1 hour and 5 minutes. The second part of the slurry was transferred on top of the filter cake and the composite was stirred briefly to homogenize the batch. The second part was filtered using about 26.1 to about 29.1 psi nitrogen pressure and the cake was pushed free of liquor after about 3 hours. The cake was washed with hot aqueous tert-butanol solution (352 kg, 5 vol.) at about 38-42° C. and 3× hot purified water (370 L, 5 vol.) at about 65-70° C.

The filter/dryer jacket temperature was set to about 43° C. and the product was dried in vacuo with periodic stirring over about 26 hours. Purity was determined to be about 99.7%. The overall yield of isolated product was about 74.4% (52.45 kg).

Batch 2

A reactor vessel was charged with methyl 3-[5-(2-fluorophenyl)-[1,2,4]oxadiazol-3-yl]-benzoate (47 kg, wet cake) and molten tert-butanol (111.4 kg). The vessel was sealed and the batch temperature was set to 30-40° C. and the agitator was started. Purified water (51.6 kg.) was charged into the vessel. This charge was followed by the addition of 3.47% w/w aqueous sodium hydroxide solution (202.4 kg). The batch temperature was raised to about 67-73° C. over about 1 hour and then stirred for about 3 hours at about 70° C.

The batch was filtered with 1 micron polypropylene filter bag under slight positive pressure of nitrogen and then transferred to a new reactor. The vessel was charged with purified water (146 kg) and the batch was heated to about 68-72° C.

The batch was charged with 10.7% aqueous hydrochloric acid over about 4 hours. The batch temperature was maintained at about 68-72° C. during the addition. The pH of the batch was determined to be about 2.2, by a pH meter and stirring at about 70° C. was continued for about an additional 1 hour.

The batch was cooled in a linear fashion from 70° C. to about 60° C. over about 2 hours. The batch at about 60° C. was cooled in a linear fashion from 60° C. to about 40° C. over about 2 hours. The batch was stirred for further 2 hours at 40° C. and the slurry was transferred into a centrifuge filter. Filtration was complete after about 30 minutes. The filter cakes were washed with about 42% w/w aqueous tert-butanol (165 kg) over about 30 minutes. Purified water (118 kg, 40° C.) was applied to the cakes as the final wash. The cakes were dried at about 900 rpm for about 1 hour and then discharged into a drum.

The wet cakes were transferred into a paddle dryer (a double-cone dryer is also suitable for this step) and the jacket temperature was set to about 70° C. The product was dried in vacuo at about 70° C. with periodic stirring over about 48 hours. Purity was determined to be about 99.8%. The overall yield of isolated product was about 74% (68.5 kg).

Batch 3

A reaction vessel was charged with methyl 3-[5-(2-fluorophenyl)-[1,2,4]oxadiazol-3-yl]-benzoate (10 g) and molten tert-butanol (128 mL). The batch temperature was set to 30-40° C. and the agitator was started. 4.48% w/w aqueous sodium hydroxide solution (32.5 g) was charged into the vessel over about 30 minutes. The batch temperature was maintained at about 40-50° C. The batch temperature was raised to about 78-82° C. over about 1 hour and then stirred for about an additional 1 hour at about 78-82° C. The batch was filtered with 5 μm polyethylene filter under slight positive pressure of nitrogen and then transferred to a new reactor. The batch temperature was maintained at about 78-82° C.

A new vessel was charged with 37% aqueous hydrochloric acid (4 mL) and molten tert-butanol (8 mL). The temperature was maintained at about 30-40° C. and the mixture was stirred for about 30 minutes.

The batch was charged with the hydrochloric acid in tert-butanol over about 4 hours using a metering pump. The first half of the charge was added over about 20-30 minutes. The agitator speed was set to about 200 rpm. The remaining charge was added over about 3.5 hours. The agitator speed was set to about 100 rpm. The batch temperature was maintained at about 78-82° C. during the addition. The pH of the final batch was adjusted to be about 1.2, by a pH meter and stirring at about 78-82° C. was continued for about an additional 1 hour.

The batch was cooled in a linear fashion from 78-82° C. to about 70° C. over about 1 hour. The batch at about 70° C. was cooled in a linear fashion from 70° C. to about 50° C. over about 4 hours and the agitator speed was set to about 80 rpm. The batch at about 50° C. was cooled in a linear fashion from 50° C. to about 40° C. over about 4 hours and the agitator speed was set to about 60 rpm. The batch was stirred for further 4 hours at 40° C.

The filter temperature was set to about 40-45° C. The slurry was transferred into a filter. Filtration was complete after about 1 minute. The filter cakes were washed with tert-butanol (50 mL, 50° C.) over about 2 minutes. Purified water (100 mL×2, 60° C.) was applied to the cakes as the final wash.

The cakes were dried at about 60-70° C. under vacuum for about 12 hours and then discharged in to a container.

HPLC purity was determined to be about 99.9% area. The yield of isolated product was about 94% (9.0 g).

3-[5-(2-fluorophenyl)-[1,2,4]oxadiazol-3-yl]-benzoic acid: One pot process

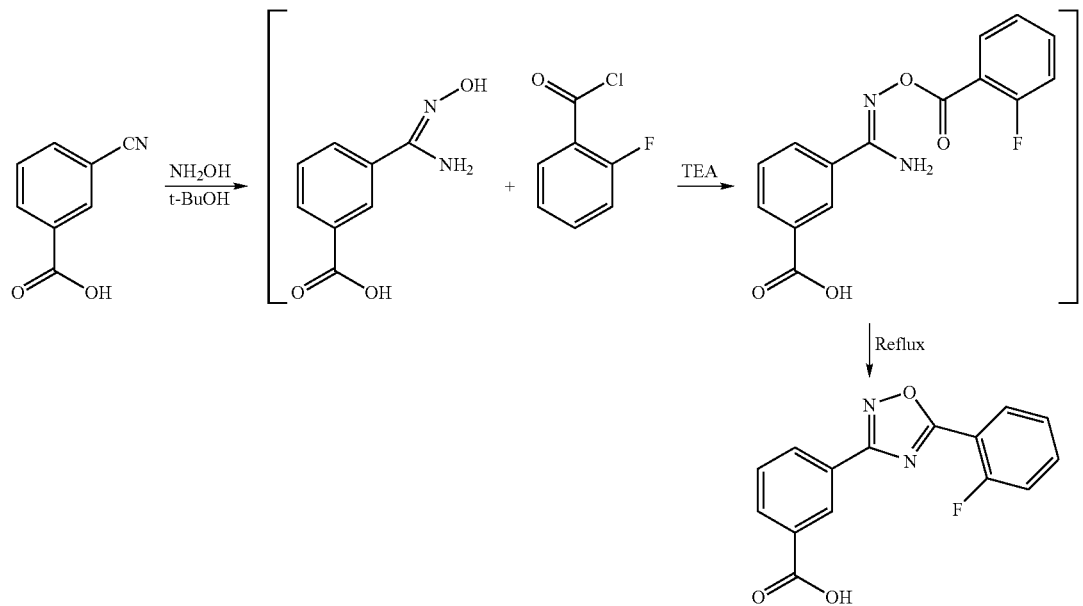

A reactor vessel was charged with 3-Cyanobenzoic acid (7.35 g) and molten tert-butanol (100 mL). The vessel was sealed and the batch temperature was set to 60° C. and the agitator was started. The suspension was stirred for 1 h and then the batch temperature was set to 40° C. 50% aqueous hydroxylamine (3.63 g) was charged to the reactor in an inert atmosphere over 3 hours. The batch temperature was maintained at 38-41° C. during the addition. The reaction was completed after stirring for 18 hours at 40° C.

The batch was cooled to 27° C. and charged with triethylamine (5.56 g) over 2 minutes. 2-Fluorobenzoyl chloride (7.82 g) was added over 3 hours. The batch temperature was maintained at 24-27° C. during the addition. The batch was stirred for further 4 hours at 40° C.

The batch was heated to 79° C. over 30 minutes and stirred for 16 hours at about 79° C. To the white suspension was added water (100 mL) over 3 hours while the batch temperature was maintained at 70° C. The batch was charged with 37% aqueous hydrochloric acid over 20 minutes. The pH of the batch was determined to be about 2.2, by a pH meter and stirring at about 70° C. was continued for about an additional 1 hour.

The batch was cooled in a linear fashion from 70° C. to 30° C. over 3 hours and the slurry was transferred into a filter. Filtration was complete after 5 minutes. The filter cakes were washed with tert-butanol (50 mL, 40° C.) over 5 minutes. Purified water (100 mL, 60° C.) was applied to the cakes as the final wash. The cakes were dried in a vacuum oven at 70° C. for 18 hour and then discharged. Purity was determined to be about 98.68%. The overall yield of isolated product was about 76% (10.8 g).

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

What is claimed is:
1. A process for preparing a compound of the formula:

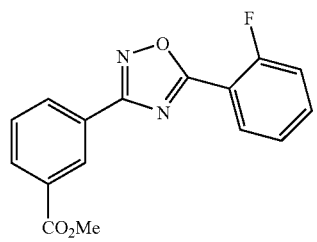 [SMILES: COC(=O)c1cccc(-c2noc(-c3ccccc3F)n2)c1]

or a pharmaceutically acceptable salt thereof, comprising performing the following steps without isolation of an intermediate:
(1) reacting the cyanobenzoic acid methyl ester:

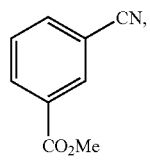

with hydroxylamine, to give:

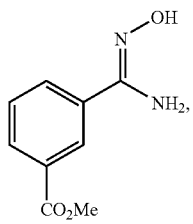

followed by (2) acylation with 2-fluorobenzoyl chloride, to give:

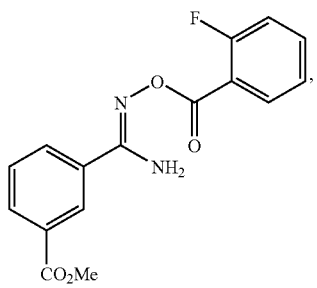 [SMILES: COC(=O)c1cccc(/C(N)=N/OC(=O)c2ccccc2F)c1]

followed by (3) condensation.

2. The process of claim 1, wherein steps (1)-(3) are carried out in the same organic solvent.

3. The process of claim 2, wherein the solvent is tert-butanol.

4. The process of claim 1, further comprising:

(4) hydrolysis of the methyl ester of a compound of the formula:

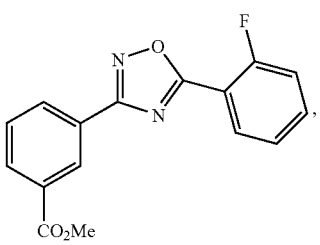

to give:

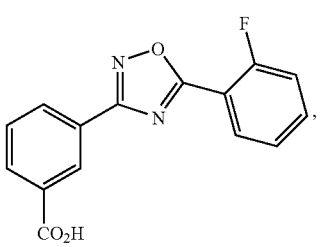 [SMILES: O=C(O)c1cccc(-c2noc(-c3ccccc3F)n2)c1]

or a pharmaceutically acceptable salt thereof.

5. A process for preparing a compound of the formula:

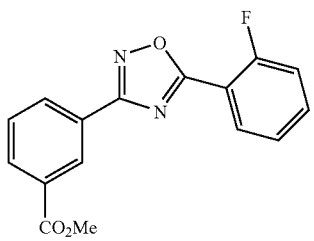 [SMILES: COC(=O)c1cccc(-c2noc(-c3ccccc3F)n2)c1]

or a pharmaceutically acceptable salt thereof, comprising performing the following steps in the same organic solvent:

(1) reacting the cyanobenzoic acid methyl ester:

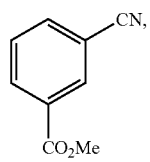

with hydroxylamine, to give:

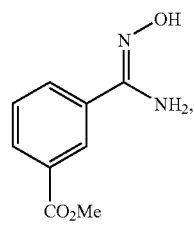

followed by (2) acylation with 2-fluorobenzoyl chloride, to give:

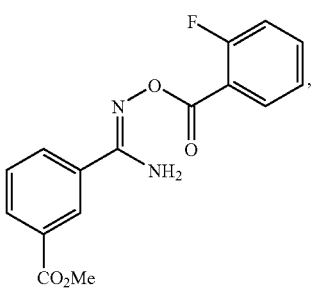 [SMILES: COC(=O)c1cccc(/C(N)=N/OC(=O)c2ccccc2F)c1]

followed by (3) condensation.

6. The process of claim 5, wherein the solvent is tert-butanol.

7. The process of claim 5, further comprising:
(4) hydrolysis of the methyl ester of a compound of the formula:
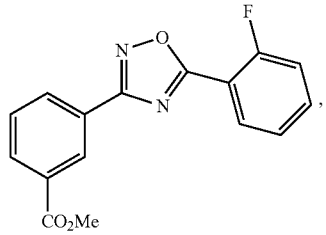 [SMILES: O=C(O)c1cccc(-c2noc(-c3ccccc3F)n2)c1]
to give:
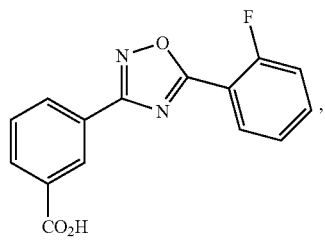
or a pharmaceutically acceptable salt thereof.
8. The process of claim 7, wherein the hydrolysis is carried out in tert-butanol.
* * * * *